United States Patent
Kane et al.

(10) Patent No.: US 11,259,757 B2
(45) Date of Patent: Mar. 1, 2022

(54) TEMPERATURE ALERT DEVICE

(71) Applicant: LIMANS 025 HOLDINGS, LLC, Miramar, FL (US)

(72) Inventors: Randy M. Kane, Clearwater, FL (US); Jeffrey Rose, Miramar, FL (US)

(73) Assignee: LIMANS 025 HOLDINGS, LLC, Miramar, FL (US)

( * ) Notice: Subject to any disclaimer, the term of this patent is extended or adjusted under 35 U.S.C. 154(b) by 0 days.

(21) Appl. No.: 17/146,695

(22) Filed: Jan. 12, 2021

(65) Prior Publication Data
US 2021/0353236 A1 Nov. 18, 2021

Related U.S. Application Data

(60) Provisional application No. 63/024,129, filed on May 13, 2020.

(51) Int. Cl.
*A61B 5/01* (2006.01)
*A61B 5/00* (2006.01)

(52) U.S. Cl.
CPC ............... *A61B 5/746* (2013.01); *A61B 5/01* (2013.01); *A61B 5/681* (2013.01); *A61B 5/7282* (2013.01); *A61B 5/7445* (2013.01); *A61B 2560/0209* (2013.01); *A61B 2560/0214* (2013.01)

(58) Field of Classification Search
CPC ........... A61B 5/746; A61B 5/01; A61B 5/681; A61B 5/7282; A61B 5/7445; A61B 2560/0209; A61B 2560/0214
See application file for complete search history.

(56) References Cited

U.S. PATENT DOCUMENTS

| | | | |
|---|---|---|---|
| 5,924,979 A * | 7/1999 | Swedlow | A61B 5/14551 600/300 |
| 9,357,929 B2 | 6/2016 | Paquet | |
| 10,295,413 B2 | 5/2019 | Balboni | |
| 2007/0161921 A1 | 7/2007 | Rausch | |
| 2012/0029308 A1 | 2/2012 | Paquet | |
| 2012/0029315 A1 * | 2/2012 | Raptis | A61B 5/0022 600/301 |
| 2012/0150062 A1 | 6/2012 | Yu | |
| 2012/0306643 A1 * | 12/2012 | Dugan | A61B 5/742 340/539.12 |
| 2017/0265781 A1 * | 9/2017 | Larson | A61B 5/0024 |
| 2018/0055457 A1 | 3/2018 | Balboni | |
| 2018/0303419 A1 * | 10/2018 | Munoz | A61B 5/0022 |
| 2019/0021595 A1 | 1/2019 | Sebban | |

* cited by examiner

*Primary Examiner* — Eric F Winakur
(74) *Attorney, Agent, or Firm* — The Concept Law Group, PA; Scott D. Smiley

(57) ABSTRACT

A system, method, and apparatus for alerting temperature is disclosed. The system includes a temperature alert device configured to be housed within a housing, wherein the device is a wearable device including at least a sensor configured to continuously collect the body temperature of the wearer and indicate the body temperature of the wearer continuously through a light emitting mechanism based on the body temperature collected by the sensor in a manner that does significantly deplete battery life of the device.

20 Claims, 13 Drawing Sheets

TEMPERATURE ALERT DEVICE

CROSS-REFERENCE TO RELATED APPLICATIONS

This application claims priority to U.S. Provisional Patent Application Ser. No. 63/024,129 filed May 13, 2020, and claims the benefit of that application, the entirety of which is hereby incorporated by reference.

FIELD OF THE INVENTION

The present invention relates generally to the field of wearable electronic devices, and more specifically to a system and method for a wearable device for alerting of body temperature of the wearer.

BACKGROUND OF THE INVENTION

Body temperatures serve as primary indicators of whether an individual is having symptoms of a fever. Although wearable devices configured to acquire various types of data associated with the wearer, such as the body temperature, have become widespread, recently the demand for assurances such as safety, sanitation, and security have become extremely high resulting in society going from desiring to collect the various types of data for personal reasons to desiring to collect the data for illustrative and validating purposes to the public. In particular, due to the emerging of global health threats, the collection and presentation of personal data is a significant factor in determining if an individual is granted access in a particular space. For example, when attempting to gain entry to a venue, individuals have their body temperature checked wherein only if the temperature falls within the normal body temperature range (97° F. to 99° F.) then the individual is granted access to the venue. Indicators such as body temperatures have become the newest tools for assurance of safety and health among the public, and will remain so for the foreseeable future.

However, a major drawback of wearable devices configured to collect user-specific data such as body temperature is not only the continuous draining of power from a battery integrated in the device, but also the large size of the battery reducing the amount of space for additional components in the device. For example, collecting data and subsequently presenting the collected data on an interface or other applicable means of presentation on the device are just a few tasks that require draining of a significant amount of battery power rendering battery capacity and longevity a major issue. Another drawback of the configurations of these devices is that they do not permit a sleek design without taking away from the efficiency of the device. Furthermore, the aforementioned devices fail to account for mechanisms that continuously collect and display current body temperatures and update the body temperatures in real-time without depleting the battery life. These aforementioned devices also fail to take into account mechanisms that acquire and analyze haptic data and kinesthetic communication; thus, resulting in frequent inaccuracies in the body temperature acquired by the devices.

Therefore, there exists a need for a device and method for collecting and alerting the temperature of the wearer in a manner that does not fall victim to the aforementioned issues associated with current wearable devices.

SUMMARY OF THE INVENTION

The invention provides a system, method, and apparatus for alerting the temperature of a user that overcomes the hereinafore-mentioned disadvantages of the heretofore-known devices and methods of this general type and that effectively facilitates collection, updating, and presentation of temperature readings without depleting significant amounts of battery power.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for alerting a temperature. The system also includes a wearable device may include a processor, a power supply, and at least one sensor, where the wearable device is configured to be in proximal contact with an animate part of a user. The at least one sensor is communicatively coupled to a light emitting mechanism wherein the at least one sensor is configured to collect an internal body temperature associated with the user in real-time, and the light emitting mechanism is configured to continuously execute a predetermined alert activity based on the processor determining the internal body temperature exceeds a predetermined threshold. Other embodiments of this aspect include corresponding computer systems, apparatus, and computer programs recorded on one or more computer storage devices, each configured to perform the actions of the methods.

One general aspect includes a wearable device for alerting a temperature. The wearable device also includes a processor, power supply, at least one sensor, and wherein the wearable device is configured to be in proximal contact with an animate part of a user. The least a sensor is communicatively coupled to a light emitting mechanism and configured to collect an internal body temperature associated with the user in real-time. The light emitting mechanism is configured to continuously execute a predetermined alert activity based on the processor determining the internal body temperature exceeding a predetermined threshold. Other embodiments of this aspect include corresponding computer systems, apparatus, and computer programs recorded on one or more computer storage devices, each configured to perform the actions of the methods.

One general aspect includes a method for alerting a temperature. The method also includes receiving, via at least one sensor in proximal contact with an animate part of a user, an internal body temperature of the user in real-time. The method also includes determining, via a processor, whether the internal body temperature falls below or exceeds a predetermined threshold. The method also includes executing, via a light emitting mechanism, a predetermined alert activity based on the determination. The method also includes executing the predetermined alert activity continuously without depleting a power source associated with the at least one sensor. Other embodiments of this aspect include corresponding computer systems, apparatus, and computer programs recorded on one or more computer storage devices, each configured to perform the actions of the methods.

Although the invention is illustrated and described herein as embodied in a system, method, and apparatus for alerting temperature, it is, nevertheless, not intended to be limited to the details shown because various modifications and structural changes may be made therein without departing from the spirit of the invention and within the scope and range of equivalents of the claims. Additionally, well-known elements of example embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely example of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
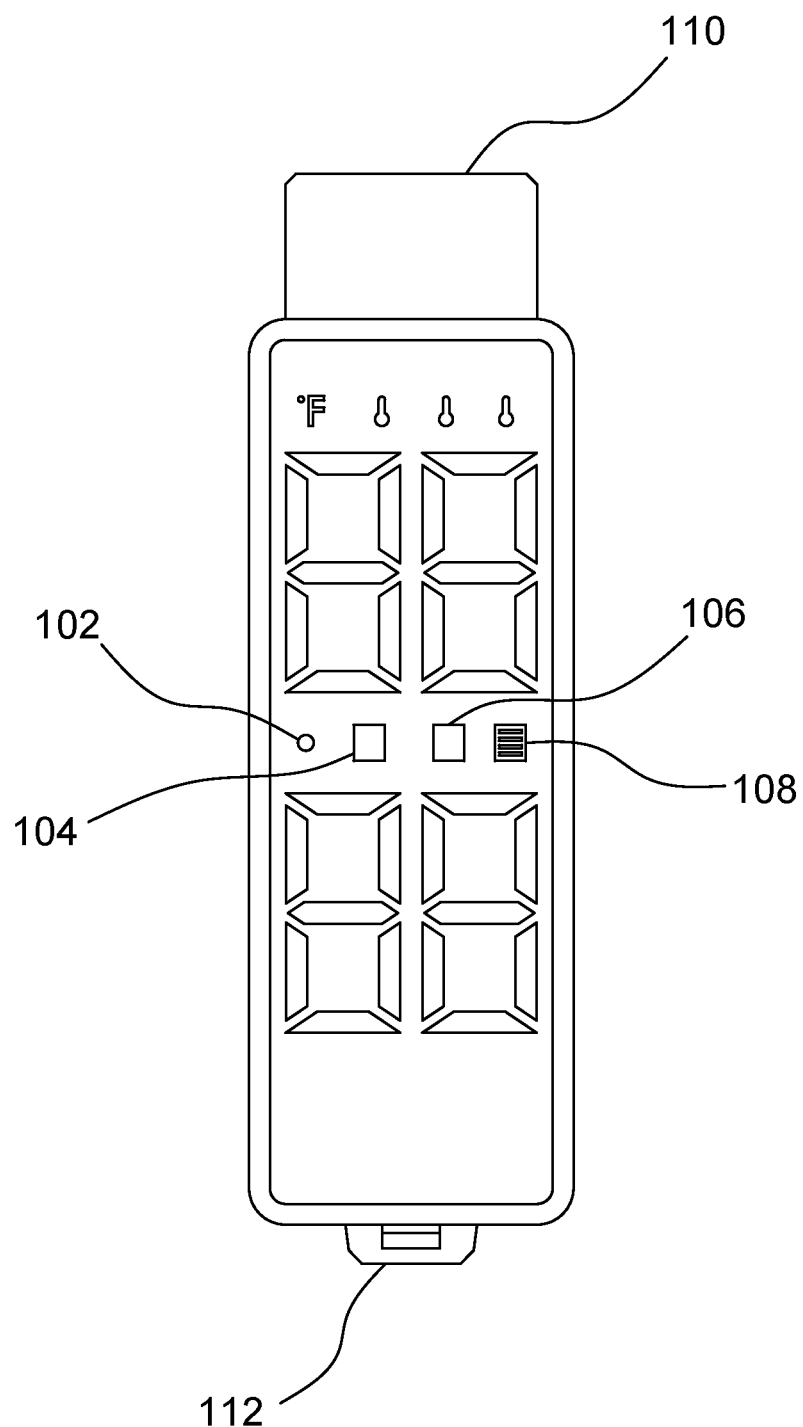
FIG. 1 is a top view of a temperature alert device, according to an example embodiment.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient system, method, and apparatus for alerting temperature. Embodiments of the invention provide a system including a temperature alert device configured to be housed within a housing, wherein the device is a wearable device configured to continuously collect the body temperature of the wearer and indicate the body temperature of the wearer continuously through a light emitting mechanism. Embodiments of the invention further provide at least a sensor disposed on the temperature alert device configured to continuously collect sensor data; in particular, temperature data and haptic data in order to not only alert the wearer of a change in body temperature in real-time, but also efficiently analyze and display the current body temperature of the wearer. Embodiments of the invention further provide a power source for the temperature alert device configured to be charged via insertion of the temperature alert device directly into the USB port and further configured to automatically adjust the operating capacity (i.e., sleep mode, power saving mode, etc.) and power usage of the temperature alert device based upon the overall power storage reading, the frequency of temperature collecting, and emitting of color-coded indicators associated with the body temperature reading. Embodiments of the invention further provide a configuration of the temperature alert device wherein the temperature alert device is configured to be removed from the housing and placed at and/or near a body cavity for a temperature reading. The systems and methods described herein provide improvements to the collection, analysis, and presentation of the body temperature of the wearer in a manner that is not only continuous and in real-time, but also avoids draining of a power source; thus, reducing the processing and hardware costs.

Referring now to FIG. 1, an illustration of a temperature alert device (hereinafter referred to as "TAD") 100 is depicted, according to an exemplary embodiment. In one embodiment, TAD 100 includes at least a sensor 102, a user interface 104, a light emitting mechanism 106, at least a power source 108, and a USB plug 110. In some embodiments, power source 108 is a rechargeable polymer lithium battery; however, power source 108 may be any applicable battery, supercapacitor, or any other power source known to those of ordinary skill in the art. In one embodiment, TAD 100 may further include a loop mechanism 112 configured to allow TAD 100 to be attached to a clasp, hook, clip, or any other applicable form of affixer that allows TAD 100 to be donned and/or carried. It is to be understood that TAD 100 may be composed of carbon steel, stainless steel, aluminum, titanium, composites, ceramics, polymeric materials such as polycarbonates, such as acrylonitrile butadiene styrene (ABS plastic), Lexan™, Makrolon™, or any other applicable material and combination thereof. In one embodiment, TAD 100 is IP67 water resistant and IP68 waterproof. It is to be understood that TAD 100 and all of its components may be manufactured from a variety of different processes including an extrusion process, a mold, welding, shearing, punching welding, folding etc. It is to be understood that sensor 102 may be a temperature sensor, haptic sensor, biometric sensor, accelerometer, gyroscope, magnetometer, global positioning system (GPS), heart rate sensor, pedometer, pressure sensor, or any combination thereof. Various shapes, sizes, and dimensions associated with TAD 100 and its components are within the scope and spirit of the disclosure. In one embodiment, user interface 104 is configured to display an analysis or direct representation of a body temperature collected by sensor 102 wherein the displaying may be a numerical representation of the temperature, a color-coded indicator emitted from light emitting mechanism 106 and/or user interface 104 associated with the temperature, or any other applicable means of displaying temperature and/or combinations thereof. In some embodiments, light emitting mechanism 106 is a light-emitting diode (LED) or any other applicable semiconductor configured to emit various colors of light at various intensities.

Figure 2:
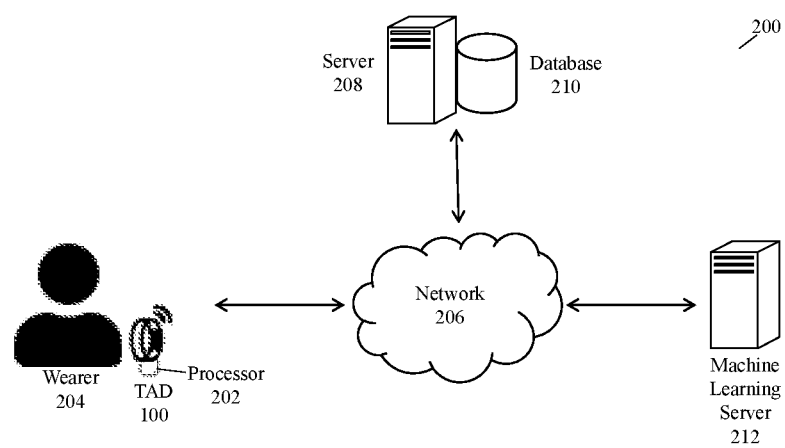
FIG. 2 is block diagram of a system for alerting temperature utilized by the temperature alert device, according to an example embodiment.

Referring now to FIG. 2, a temperature alert system 200 for TAD 100 is depicted, according to an exemplary embodiment. In one embodiment, system 200 includes a processor 202 allocated to TAD 100, a wearer 204 wherein TAD 100 is affixed to and associated with wearer 204, a communications network 206, a server 208 communicatively coupled to a database 210, and a machine learning server 212. It is to be understood that processor 202, server 208, and machine learning server 212 are communicatively coupled to each other in which data acquired from sensor 102 is communicated over network 206. It is to be understood that system 200 is not required in order for TAD 100 to perform its inherent functions; however, system 200 may be utilized in order to perform collection, analysis, and distribution of data derived from sensor 102. In one embodiment, server 208 is configured to generate a centralized platform including one or more interfaces for wearer 204 to view metrics, analytics, and micro-analytics associated with the data collected by sensor 102 in real-time.

In one embodiment, sensor 102 is configured to be allocated on any applicable surface of TAD 100 that allows direct and/or proximate contact with the skin surface of the wearer 204. In one embodiment, processor 202 is configured to be communicatively and/or electrically coupled to the aforementioned components of TAD 100, wherein the processor 202 is configured to be a low-power processor designed to manage high-speed and low-speed circuitry allowing TAD 100 to operate in an efficient manner without entirely depleting power source 108. In some embodiments, TAD 100 may further include a vibration motor (not shown) communicatively coupled to the processor 202 configured to serve as a source of one or more alerting vibrations to be felt by the wearer in addition to a mechanism for applying kinesthetic communication, 3D touch, and/or haptic data feedback. The vibration motor is configured to be activated for the purpose of utilizing the haptic data feedback and alerting vibrations to inform the wearer of a significant change of body temperature. For example, if processor 202 detects a change of body temperature, via the sensor data collected by sensor 102, from a normal body temperature to an abnormally high body temperature then processor 202 instructs the vibration motor to notify wearer 204 via the one or more alerting vibrations.

In one embodiment, light emitting mechanism 106 is a plurality of light emitting diodes (LEDs) communicatively or electrically coupled to the processor 202 wherein light emitting mechanism 106 is configured to emit light at various intensities based upon the current battery capacity of power source 108, wherein in some embodiments, the battery capacity of power source 108 is 75 mAh 3.7 v. In one embodiment, sensor 102, light emitting mechanism 106, and the processor 202 act in cooperation in order to collect temperature data of the wearer via sensor 102, analyze and/or process the temperature data via processor 202, and present an indicator of the temperature data via the light emitting mechanism 106. Light emitting mechanism 106 is further configured to emit various colors, patterns, movements of light, or any other presentation of light that depicts distinct functionality/modes based on determinations by the processor 202 relating to the temperature data. For example, sensor 102 collects temperature data and the processor 202 analyzes that the temperature data is abnormally high indicating that the wearer has a fever in which the processor 202 instructs light emitting mechanism 106 to continuously emit a red light at a designated intensity.

It is to be understood that TAD 100 is configured to be communicatively coupled to server 208, via processor 202, allowing sensor data acquired from sensor 102 to be transmitted to server 208 and machine learning server 212 over network 206. Network 206 may be a communications network such as but not limited to a Local Area Network (LAN), Wide Area Network (WAN), mobile communication network (GSM, GPRS, CDMA, MOBITEX, EDGE), Ethernet or the Internet, one or more terrestrial, satellite or wireless links, or any applicable medium or mechanism for flowing of information. In one embodiment, machine learning server 212 may utilize one or more machine learning algorithms in order to generate predictions relating to data received by sensor 102. For example, in addition to the current temperature of wearer 204, sensor 102 collects a plurality of haptic data configured to be transmitted to machine learning server 212 via processor 202 for machine learning server 212 to apply one or more machine learning algorithms to the collected data in order to infer contact location and normal forces for multiple-contact points in addition to other applicable predictions associated with the body temperature of wearer 204. For example, machine learning server 212 may generate a deep learning model based on training data (derived from data collected by sensor 102) utilizing the one or more aforementioned machine learning techniques, wherein the feature values are configured to be inserted into the deep learning model. It is the objective of machine learning server 212 to utilize data acquired from sensor 102 to not only provide more accurate predictions of the body temperature of wearer 204, but also to assist the facilitation of applying the one or more alerting vibrations once processor 202 detects exceeding or failing to satisfy any threshold provided throughout this disclosure.

Figure 3:
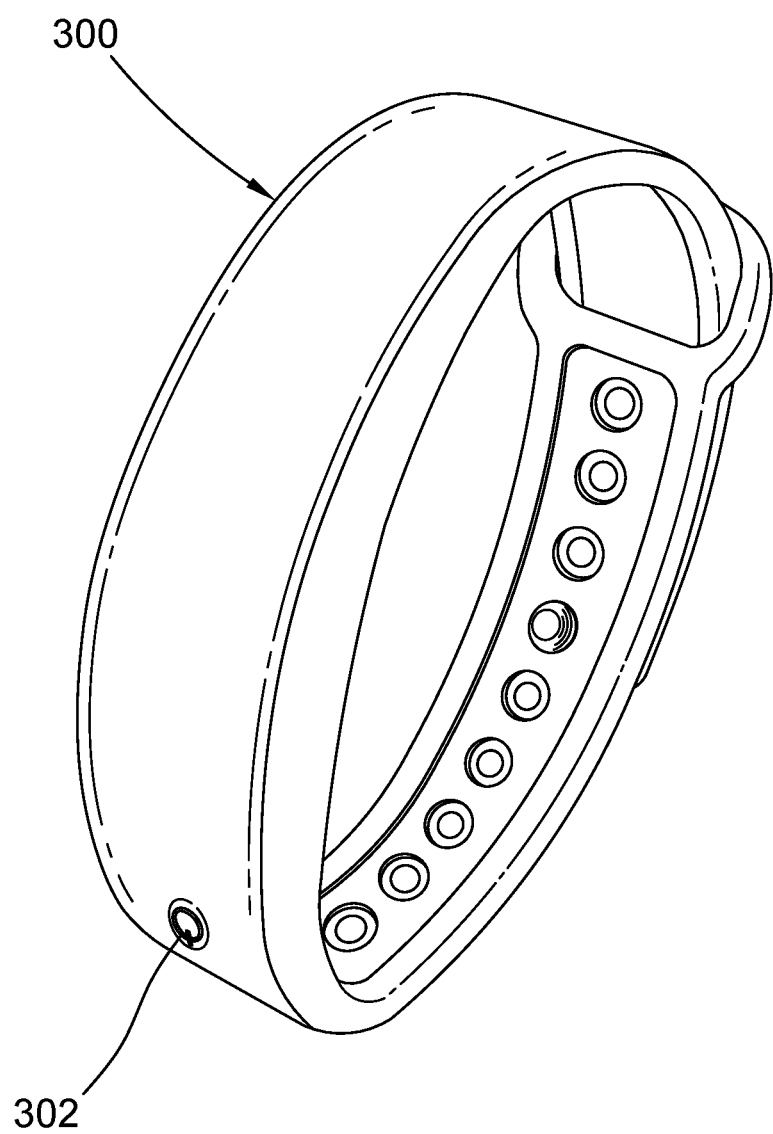
FIG. 3 is a prospective view of the temperature alert device within a housing, according to an example embodiment.

Referring now to FIG. 3, TAD 100 is presented within a housing 300 in an affixed position, according to an exemplary embodiment. It is to be understood that housing 300 may be a wearable housing configured to be affixed to wearer 204 in a manner that allows sensor 102 to be in direct contact with an animate part of wearer 204 such as, but not limited to, the wrist, neck, umbilicus, axilla, tympanum, or any other applicable part of the wearer configured to be interacted with to receive an accurate temperature reading. In some embodiments, housing 300 may be a wristband, anklet, necklace, earring, or any other applicable wearable configured to be donned by the wearer while simultaneously being in direct or proximate contact with an animate part of the wearer. It is to be understood that TAD 100 is not limited to human beings and in some embodiments may be affixed to pets, livestock, or any other applicable subjects in order to accurately read and present the temperature of wearer 204 in real-time. It is to be understood that TAD 100 may be permanently housed and/or amalgamated in housing 200; however, in preferred embodiments, TAD 100 is designed and configured to be detached from housing 300 for various purposes such as removing TAD 100 from housing 300 for charging TAD 100. Other purposes for removing TAD 100 from housing 300 include but is not limited to inserting USB plug 110 into a USB port; however, in light of embodiments supporting other configurations for charging power source 108 purposes such as solar energy charging, induction charging, or any other applicable form of charging of a power source known to those of ordinary skill in the art are within the spirit and scope of the disclosure. In some embodiments, TAD 100 may be removed and/or extracted from housing 300 in order to be applied by wearer 204 at and/or near a body cavity in order to get an exact temperature from the body cavity via sensor 102. In some embodiment, housing 300 may be composed of rubber, thermoplastic elastomers, plastic, silicon, or any other applicable wearable material, and/or combination thereof that supports stretching and adaptability to come into contact with the animate parts of the wearer.

It is to be understood that housing 300 is configured to serve as a retentive covering of TAD 100 wherein in some embodiments housing 300 is designed to be composed of transparent or semi-transparent material allowing user interface 104 and light emitting mechanism 106 to be visible to the wearer when TAD 100 is retained in housing 300. In one embodiment, housing 300 may include a power toggle 302 configured to be placed directly on a portion of TAD 100 that facilitates powering TAD 100 on and off and/or transitioning TAD 100 into a reduced capacity (i.e, sleep mode, power saving mode, etc.). In one embodiment, housing 300 further includes a fastener means including a male component and a female component configured to be coupled, and may be configured to be adjustable based upon the tightness or looseness preference of wearer 204. In one embodiment, the fastener means includes a prong extending outwardly from the male component configured to interlace with at least one of a plurality of fitting holes for retention. It is to be understood that TAD 100 is configured to provide the most accurate body temperature reading when sensor 102 is in direct and/or proximate contact with either an animate body part or body cavity of wearer 204.

Figures 4, 4A:
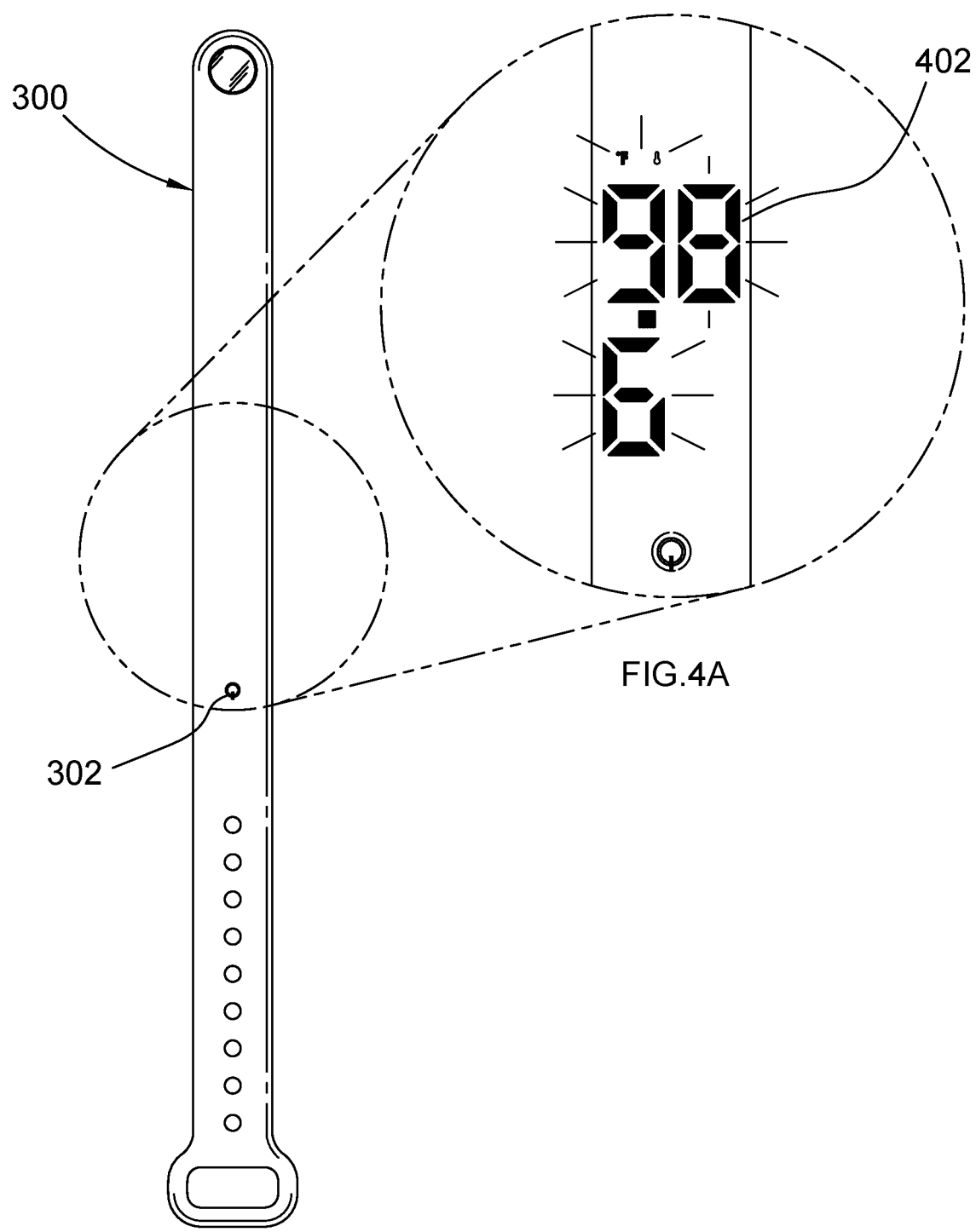
FIG. 4 is a top view of the temperature alert device within the housing in an unaffixed position, according to an example embodiment.
FIGS. 4A-4D are a depiction of user interfaces of the temperature alert device illustrating various body temperatures, according to an example embodiment.
Figure 4A:
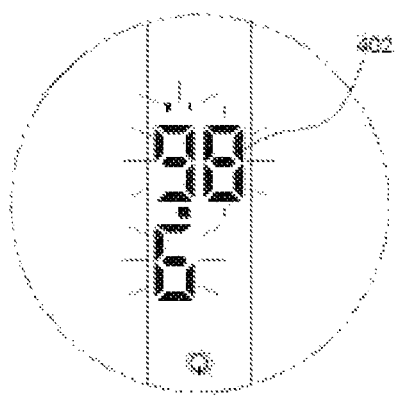
Figure 4B:
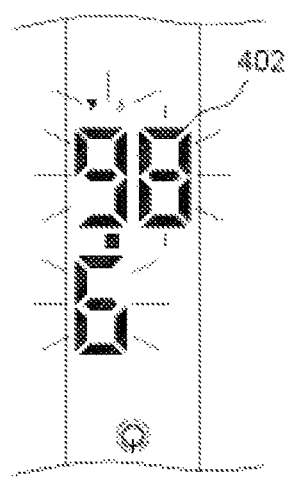
Figure 4C:
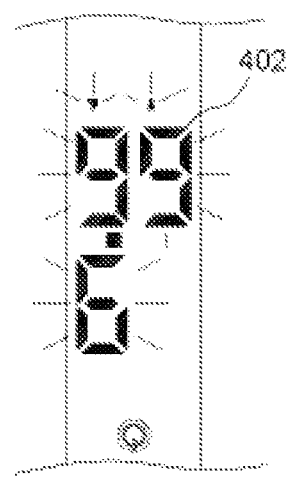
Figure 4D:
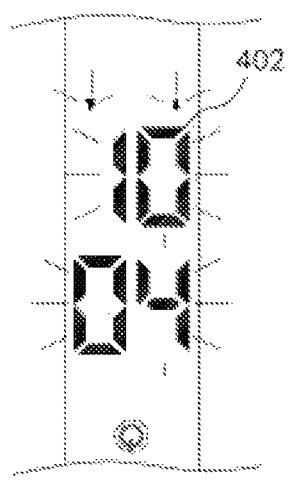

Referring now to FIGS. 4-4D, TAD 100 is presented within housing 300 in an unaffixed position (unaffixed from wearer 204), according to an exemplary embodiment. It is to be understood that the reading of a body temperature reading 402 acquired by sensor 102 is configured to be displayed externally on housing 300 via user interface 104 in real-time as illustrated in FIG. 4A. In one embodiment, processor 202 determines a plurality of body temperature thresholds associated with the data acquired from sensor 102, wherein a first body temperature threshold includes a body temperature ranging from 94° f to 99.5° f (normal body temperature) as illustrated in FIG. 4B depicting body temperature reading 402 at 98.6° f, a second body temperature threshold includes a body temperature ranging from 99.6° f to 100.3° f (high body temperature) as illustrated in FIG. 4C depicting temperature reading 402 at 99.6° f, and a third body temperature threshold includes a body temperature exceeding 100.3° f (abnormally high body temperature) as illustrated in FIG. 4D depicting body temperature reading 402 at 100.4° f. It is to be understood that the plurality of body temperature thresholds may vary based upon the body part of wearer 204 in which sensor 102 is receiving the body temperature in real-time. For example, the first body temperature threshold may include a body temperature ranging from 96.4° f to 100.4° f if the body temperature is being collected from the ear of wearer 204; however, the first body temperature threshold may also include a body temperature ranging from 95.9° f to 99.5° f if the body temperature is being collected from the mouth of wearer 204. It is to be understood that based upon the aforementioned body temperature thresholds being exceeded, processor 202 is configured to activate light emitting mechanism 106 to emit the respective color-based indicator, wherein the color-based indicator associated with the first body temperature threshold is green, the color-based indicator associated with the second body temperature threshold is amber, and the color-based indicator associated with the third body temperature threshold is red. It is to be understood that other colors, patterns, and other applicable distinguishing indicators are within the scope and spirit of the disclosure.

In one embodiment, body temperature reading 402 is continuously displayed from user interface 104 simultaneously with the color-coded indicator wherein processor 202 is configured to stop emitting body temperature reading 402 from user interface 104 and emit only the color-coded indicator from light emitting mechanism 106 based upon processor 202 detecting power source 108 beneath a power threshold wherein the power threshold is configured to be set by wearer 204 or the manufacturer. For example, body temperature reading 402 may stop being emitted from user interface 104 once processor 202 determines that power source 108 has fallen beneath a power threshold of 50% of power source 108 overall; however, processor 202 is configured to automatically adjust the intensity of the color-coded indicator based on processor 202 determining to preserve battery life. In one embodiment, emitting of body temperature reading 402 on user interface 104 is performed at predetermined time intervals subject to the default configurations and/or the preferences of the wearer, or in some embodiments, emitting of body temperature reading 402 is based on a timer operated by processor 202. For example, processor 202 may determine that user interface 104 displays body temperature reading 402 every 15 minutes and/or every instance where there is a change in the body temperature acquired from sensor 102 wherein processor 202 activates the vibration motor to provide the one or more alerting vibrations and the current color-coded indicator is configured to change to the color-coded indicator reflecting the newly acquired body temperature reading 402, wherein the transition and emitting from one color to another is performed by light emitting mechanism 106 in seamless a manner that does not draw significant power from power source 108. For example, initially TAD 100 may be emitting an amber color-coded indicator from light emitting mechanism 106 due to body temperature reading 402 displaying a temperature of 99.7° f, but once sensor 102 detects an increase in body temperature reading 402 to 100.4° f, processor 202 simultaneously instructs the vibration motor to be activated allowing wearer 204 to experience the one or more vibrations and light emitting mechanism 106 to transition from emitting the amber color-coded indicator to the red color-coded indicator. In one embodiment, TAD 100 operates to display body temperature reading 402 and the associated color-coded indicator (color associated with the applicable temperature range) for a predetermined time period. It is to be understood that the aforementioned timer is a component of processor 202 and is configured to be utilized on at least one of sensor 102, light emitting mechanism 106, power source 108, and/or the vibration motor to preserve the battery life of power source 108.

It is to be understood that the distribution of power from power source 108 along with the frequency and intensity of said distribution is determined by processor 202 wherein the processor 202 is configured to perform one or more algorithms in order to not only ensure optimization of battery life associated with power source 108, but also establish the aforementioned predetermined time intervals and power thresholds for activating certain activities on TAD 100. Examples of said one or more algorithms and/or approaches for reducing battery draining of power source 108 include but is not limited to Change Point-based Activity Monitoring (CPAM) algorithms, transmission power control-based energy-efficient (ETPC) algorithms, adjusting duty cycles associated with sensor 102, distributing computation between TAD 100 and server 208 when data is transmitted for analysis purposes, dynamically adjusting parameters (sampling frequency and classifier features), and any other applicable power-saving algorithms known to those of ordinary skill in the art.

In one embodiment, processor 202 includes an energy preservation mode configured to reduce operational capacity of power supply 108 based upon processor 202 detecting a lack of change of the internal body temperature for a time period exceeding a predetermined time threshold, wherein the predetermined time threshold is determined by processor 202 or wearer 204.

Figure 5:
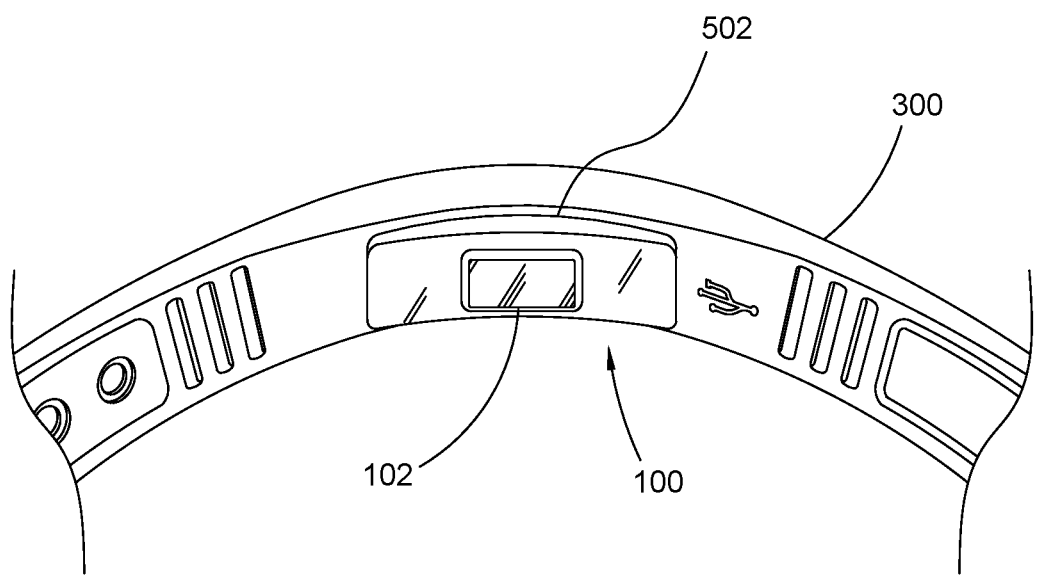
FIG. 5 is a bottom view of the housing retaining the temperature alert device, according to an example embodiment.
Figure 6:
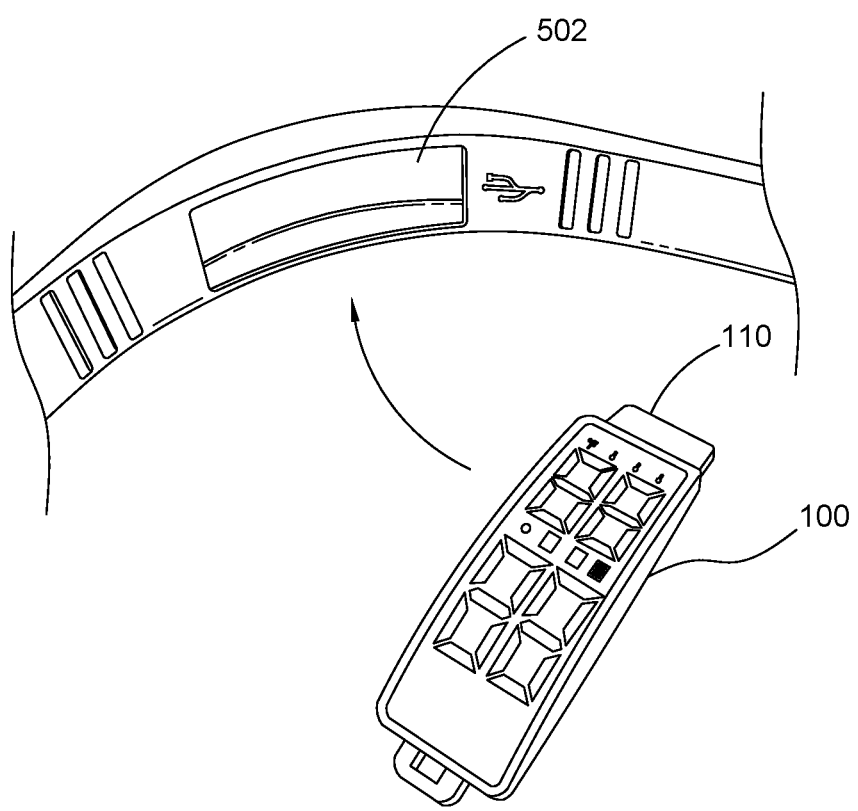
FIG. 6 is a bottom view of the housing with the temperature alert device unattached, according to an example embodiment.
Figure 7:
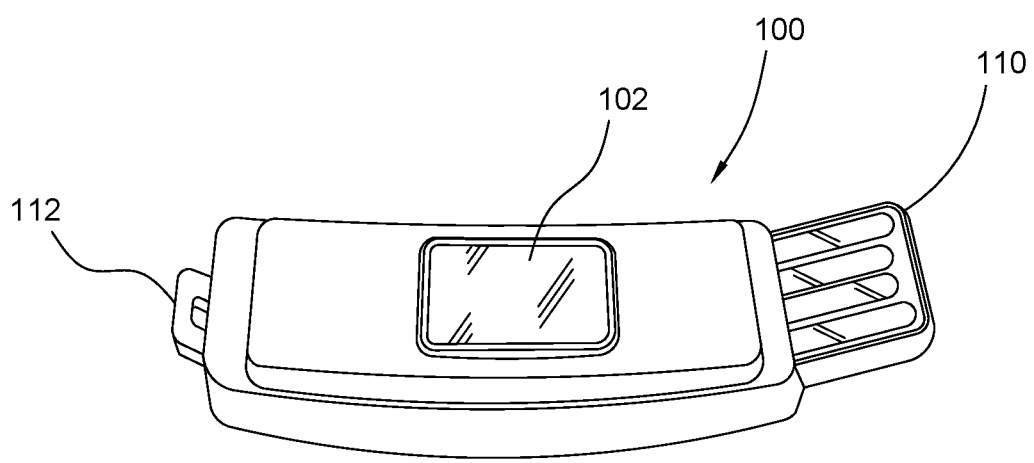
FIG. 7 is a top view of a sensor allocated on a bottom surface of the temperature alert device, according to an example embodiment.

Referring now to FIGS. 5-7, a bottom-view of TAD 100 is depicted within housing 300, according to an exemplary embodiment. In one embodiment, housing 300 further includes at least an interior opening 502 configured to expose at least a portion of TAD 100 when housed within housing 300 allowing TAD 100 to be safely and securely retained in housing 300 and easily removable from housing 300 upon the wearer extracting TAD 100 via interior opening 502. In some embodiments, housing 300 further includes an exterior opening allocated on a top/front-side of housing 300 shaped and sized to allow TAD 100 to be housed in housing 300 in addition to allowing user interface 104 and light emitting mechanism 106 to be viewed directly by wearer 204 as opposed to having the transparent or semi-transparent material of housing 300 cover user interface 104 and light emitting mechanism 106. In one embodiment, TAD 100 includes a plurality of operating modes that include but are not limited to full operational mode, reduced operational mode, extracted mode (TAD 100 outside of housing 300 for temperature reading purposes), charging mode, and any other applicable mode for sustaining temperature alerting and battery longevity. It is to be understood that activation of the aforementioned plurality of operating modes is based upon either a determination by processor 202 or manual inputs by wearer 204, wherein the determination by processor 202 is based on factors such as but not limited to the current battery capacity of power source 108, the intensity of light emitting mechanism 106 emitting the color-coded indicator, the frequency of sensor 102 collecting the body temperature from wearer 204, the frequency and/or intensity of vibration motor generating the one or more alerting vibrations, and any other applicable power consuming factor. It is to be understood that TAD 100 is intended to be housed in housing 300 as illustrated in FIG. 5 wherein the color-coded indicator being emitted by light emitting mechanism 106 is continuously emitted and projected resulting in the body temperature of wearer 204 being visible to themselves and third parties/the public. In one embodiment, sensor 102 is positioned at or near interior opening 502 allowing sensor 102 to be in direct contact with the applicable animate body part of wearer 204 while affixed to wearer 204.

Figure 8:
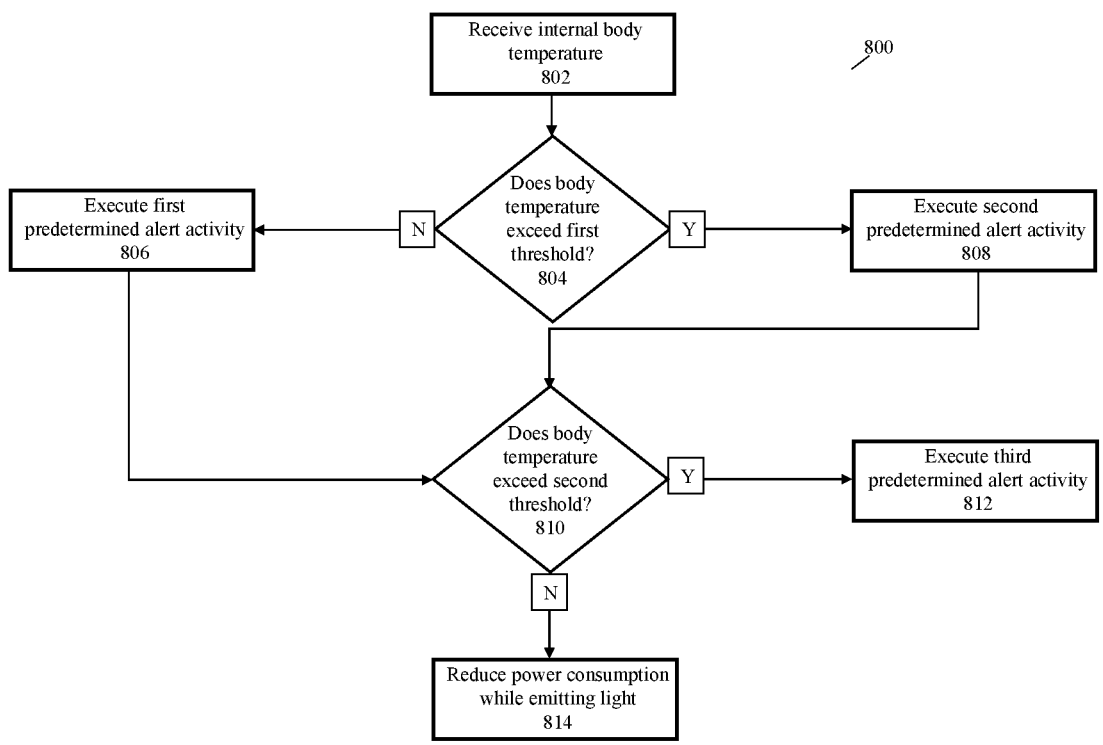
FIG. 8 is a block diagram illustrating an exemplary method for managing and monitoring authenticity and productivity in a worksite, according to an example embodiment.

Referring now to FIG. 8, a method for alerting body temperature 800 performed by TAD 100 is depicted, according to an exemplary embodiment. At step 802, sensor 102 receives a body temperature reading from the animate part of wearer 204. At step 804, processor 202 makes a determination as to whether the body temperature reading exceeds the first body temperature threshold at 99.5° f in which if not then step 806 occurs in which processor 202 performs a first predetermined alert activity in which processor 202 activates light emitting mechanism 106 wherein the green color-coded indicator illuminates from light emitting mechanism 106. Otherwise, step 808 occurs in which processor 202 performs a second predetermined alert activity in which processor 202 activates light emitting mechanism 106 wherein the amber color-coded indicator illuminates from light emitting mechanism 106. In some embodiments, TAD 100 is continuously receiving sensor data from sensor 102 and light emitting mechanism 106 is continuously emitting the applicable color-coded indicator. At step 810, processor 202 makes a determination as to whether the body temperature reading exceeds a second body temperature threshold at 100.3° f in which if the second body temperature threshold is exceeded then step 812 occurs in which processor 202 performs a third predetermined alert activity by instructing light emitting mechanism 106 to emit the red color-coded indicator. Otherwise, step 814 occurs in which light emitting mechanism 106 continues to emit the amber color-coded indicator; however, subject to the discretion of processor 202 and the current battery life associated with power source 108, processor 202 may utilize the aforementioned mechanisms to reduce the amount of power being used to either portray body temperature reading 402 on user interface 104 and/or emit color-coded indicator at a lower intensity in order to preserve battery power.

Figure 9:
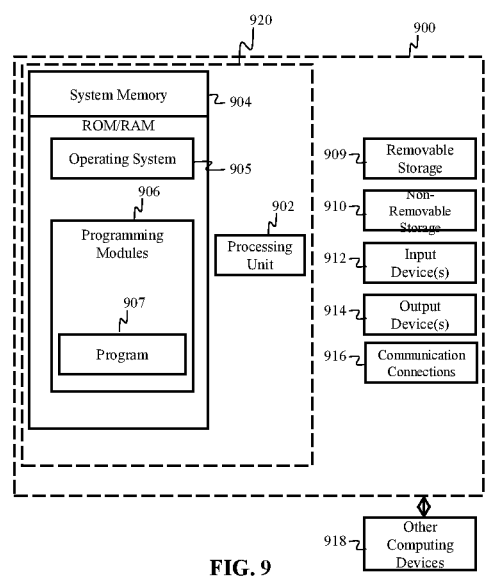
FIG. 9 illustrates a computer system according to exemplary embodiments of the present technology.

FIG. 9 is a block diagram of a system including an example computing device 900 and other computing devices. Consistent with the embodiments described herein, the aforementioned actions performed by processor 202 may be implemented in a computing device, such as the computing device 900 of FIG. 9. Any suitable combination of hardware, software, or firmware may be used to implement the computing device 900. The aforementioned system, device, and processors are examples and other systems, devices, and processors may comprise the aforementioned computing device. Furthermore, computing device 900 may comprise an operating environment for TAD 100 and process/method 800. Process 800, and data related to said processes may operate in other environments and are not limited to computing device 900.

In a basic configuration, computing device 900 may include at least one processing unit 902 and a system memory 904. Depending on the configuration and type of computing device, system memory 904 may comprise, but is not limited to, volatile (e.g. random access memory (RANI)), non-volatile (e.g. read-only memory (ROM)), flash memory, or any combination or memory. System memory 904 may include operating system 905, and one or more programming modules 906. Operating system 905, for example, may be suitable for controlling computing device 900's operation. In one embodiment, programming modules 906 may include, for example, a program module 907 for executing the actions of processor 202, for example. Furthermore, embodiments of the invention may be practiced in conjunction with a graphics library, other operating systems, or any other application program and is not limited to any particular application or system. This basic configuration is illustrated in FIG. 9 by those components within a dashed line 920.

Computing device 900 may have additional features or functionality. For example, computing device 900 may also include additional data storage devices (removable and/or non-removable) such as, for example, magnetic disks, optical disks, or tape. Such additional storage is illustrated in FIG. 9 by a removable storage 909 and a non-removable storage 910. Computer storage media may include volatile and nonvolatile, removable and non-removable media implemented in any method or technology for storage of information, such as computer readable instructions, data structures, program modules, or other data. System memory 904, removable storage 909, and non-removable storage 910 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 900. Any such computer storage media may be part of device 900. Computing device 900 may also have input device(s) 912 such as a keyboard, a mouse, a pen, a sound input device, a camera, a touch input device, etc. Output device(s) 914 such as a display, speakers, a printer, etc. may also be included. The aforementioned devices are only examples, and other devices may be added or substituted.

Computing device 900 may also contain a communication connection 916 that may allow device 900 to communicate with other computing devices 918, such as over a network in a distributed computing environment, for example, an intranet or the Internet. Communication connection 916 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 904, including operating system 905. While executing on processing unit 902, programming modules 906 (e.g. program module 907) may perform processes including, for example, one or more of the stages of the process 800 as described above. The aforementioned processes are examples, and processing unit 902 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

The claims appended hereto are meant to cover all modifications and changes within the scope and spirit of the present invention.

What is claimed is:

1. A system for alerting a temperature comprising:
   a wearable device comprising a processor, a power supply, and at least one sensor, wherein the wearable device is configured to be in proximal contact with an animate part of a user;
   wherein the at least one sensor is communicatively coupled to a light emitting mechanism;
   wherein the at least one sensor is configured to collect an internal body temperature associated with the user in real-time; and
   wherein the light emitting mechanism is configured to continuously execute a predetermined alert activity in response to the processor determining the internal body temperature exceeding a predetermined threshold of a first predetermined threshold of 94° F., a second predetermined threshold of 99.6° F., and a third predetermined threshold of 100.4° F., wherein the predetermined alert activity is different for each of the first, second, and third predetermined thresholds.

2. The system of claim 1, wherein the predetermined alert activity is a specific color being emitted from the light emitting mechanism [based on the internal body temperature falling below, within, or exceeding] for the first, second, and third predetermined thresholds, respectively.

3. The system of claim 1, wherein the light emitting mechanism emitting green, amber, and red for the first, second, and third predetermined thresholds, respectively.

4. The system of claim 1, wherein the least one sensor is configured to collect the internal body temperature continuously at a plurality of predetermined time intervals.

5. The system of claim 1, wherein the processor is configured to adjust an intensity of the predetermined alert activity based on a charge status of the power supply.

6. The system of claim 1, the processor comprising an energy preservation mode configured to reduce operational capacity of the power supply based upon the processor detecting a lack of change of the internal body temperature for a time period exceeding a predetermined time threshold.

7. The system of claim 1, wherein the power source is a 75 mAh 3.7 volt battery.

8. The system of claim 1, further comprising a digital interface configured to display the internal body temperature and a current digital time.

9. The system of claim 1, wherein the processor, the power supply, and the at least one sensor are integrated in a device and includes a charging tab that extends from the device, and wherein the device fits into and is retained in an interior opening of a wearable housing composed of at least a portion of wearable material.

10. A wearable device for alerting a temperature comprising:
   a processor;
   a power supply coupled to the processor;
   and at least one sensor, wherein the wearable device is configured to be in proximal contact with an animate part of a user and configured to collect an internal body temperature associated with the user in real-time, and wherein the at least one sensor is operably coupled to the processor;
   a light emitting mechanism operably coupled to the processor; and
   wherein the processor is configured to control the light emitting mechanism to continuously execute a predetermined alert activity in response to the processor determining the internal body temperature exceeding a predetermined threshold as indicated by the at least one sensor and based on a location of the sensor on the user, wherein the predetermined alert activity indicates a range of a plurality of ranges in which the internal body temperature fall, wherein the plurality of ranges includes at least one range that is above a normal body temperature range.

11. The wearable device of claim 10, wherein the predetermined alert activity is a specific color being emitted from the light emitting mechanism based on the internal body temperature exceeding the predetermined threshold.

12. The wearable device of claim 10, wherein the predetermined threshold comprises a plurality of predetermined thresholds wherein a first predetermined threshold is 94° F., a second predetermined threshold is 99.6° F., and a third predetermined threshold is 100.4° F. resulting in the light emitting mechanism emitting green, amber, and red respectively.

13. The wearable device of claim 10, wherein the least one sensor is configured to collect the internal body temperature continuously at a plurality of predetermined time intervals.

14. The wearable device of claim 10, wherein the processor is configured to adjust the predetermined alert activity based on the processor detecting a change of the internal body temperature outside of the predetermined threshold.

15. The wearable device of claim 10, the processor comprising an energy preservation mode configured to reduce operational capacity of the power supply based upon the processor detecting a lack of change of the internal body temperature for a time period exceeding a predetermined time threshold.

16. The wearable device of claim 10, wherein the power source is a 75 mAh 3.7 volt battery.

17. The wearable device of claim 10, further comprising a digital interface configured to display the internal body temperature and a current digital time.

18. The wearable device of claim 10, wherein the processor, the power supply, and the at least one sensor are integrated in a housing pluggable into a universal serial bus port, and wherein the housing is amalgamated into an at least partially made of rubber covering.

19. A method for alerting a temperature comprising:
   receiving, at a temperature alert device via at least one sensor of the temperature alert device that is in proximal contact with an animate part of a user, an internal body temperature of the user in real-time;
   determining, via a processor of the temperature alert device, whether the internal body temperature falls below or exceeds a predetermined threshold;
   executing, via a light emitting mechanism of the temperature alert device, a predetermined alert activity based on the determination; and
   wherein executing the predetermined alert activity is performed by adjusting an intensity of predetermined alert activity based on a battery status of a battery of the temperature alert device.

20. The method of claim 19, further comprising:
   extracting the least one sensor from a housing; and
   applying the at least one sensor to a body cavity to receive the internal body temperature of the user in real-time.

* * * * *